US012797312B2

(12) United States Patent
Ribas Quer et al.

(10) Patent No.: US 12,797,312 B2
(45) Date of Patent: Nov. 17, 2026

(54) BREAKABLE GALENIC CAPSULE

(71) Applicant: Fingerclik, S.L., Les Franqueses del Vallès (ES)

(72) Inventors: Maria Teresa Ribas Quer, Les Franqueses del Vallès (ES); José María Rodríguez Tejero, Les Franqueses del Vallès (ES)

(73) Assignee: Fingerclik, S.L., Les Franqueses del Vallès (ES)

( * ) Notice: Subject to any disclaimer, the term of this patent is extended or adjusted under 35 U.S.C. 154(b) by 856 days.

(21) Appl. No.: 17/800,570

(22) PCT Filed: Feb. 17, 2021

(86) PCT No.: PCT/ES2021/070112

§ 371 (c)(1),
(2) Date: Aug. 18, 2022

(87) PCT Pub. No.: WO2021/165558

PCT Pub. Date: Aug. 26, 2021

(65) Prior Publication Data

US 2023/0139406 A1 May 4, 2023

(30) Foreign Application Priority Data

Feb. 19, 2020 (ES) ................................ P202030143

(51) Int. Cl.

| | |
|---|---|
| ***A61K 8/11*** | (2006.01) |
| ***A61K 8/02*** | (2006.01) |
| ***A61K 8/19*** | (2006.01) |
| ***A61K 8/30*** | (2006.01) |
| ***A61K 8/72*** | (2006.01) |
| ***A61K 8/92*** | (2006.01) |
| ***A61Q 19/00*** | (2006.01) |

(52) U.S. Cl.

CPC .............. *A61K 8/11* (2013.01); *A61K 8/0216* (2013.01); *A61K 8/19* (2013.01); *A61K 8/30* (2013.01); *A61K 8/72* (2013.01); *A61K 8/922* (2013.01); *A61Q 19/00* (2013.01); *A61K 2800/10* (2013.01); *A61K 2800/41* (2013.01); *A61K 2800/594* (2013.01)

(58) Field of Classification Search

CPC ........................................................ A61K 8/11

See application file for complete search history.

(56) References Cited

U.S. PATENT DOCUMENTS

| | | | | |
|---|---|---|---|---|
| 9,949,920 B2 * | 4/2018 | Hakim | ................. | A61K 8/9794 |
| 10,015,984 B2 * | 7/2018 | Kondo | ................... | A24D 3/061 |
| 10,299,996 B2 * | 5/2019 | Weissbrodt | ............ | A61K 8/731 |
| 2009/0208568 A1 * | 8/2009 | Hannetel | ................ | A61Q 19/00 426/89 |
| 2018/0325785 A1 * | 11/2018 | Ishiwatari | ................ | A61K 9/50 |

FOREIGN PATENT DOCUMENTS

| | | | | |
|---|---|---|---|---|
| FR | 3122575 A1 * | 11/2022 | ............... | A61K 8/73 |
| WO | WO-2007012981 A2 * | 2/2007 | ........... | A23L 1/0029 |

* cited by examiner

*Primary Examiner* — Gina C Justice

(57) ABSTRACT

The present invention falls within the general field of cosmetics, and in particular, it relates to a breakable capsule (1) with a membrane (2) and core (3) suitable for releasing an active ingredient comprised in the membrane (2), both for cosmetic use and for pharmaceutical use and to the preparation processes thereof. The capsule (1) has good chemical and mechanical stability wherein the capsule, once applied to the skin, reduces or does not generate residues and, at the same time, any residual trace produced by the membrane (2) can be absorbed or adsorbed by the skin. In addition, they have good stability against light and breakage.

16 Claims, 1 Drawing Sheet

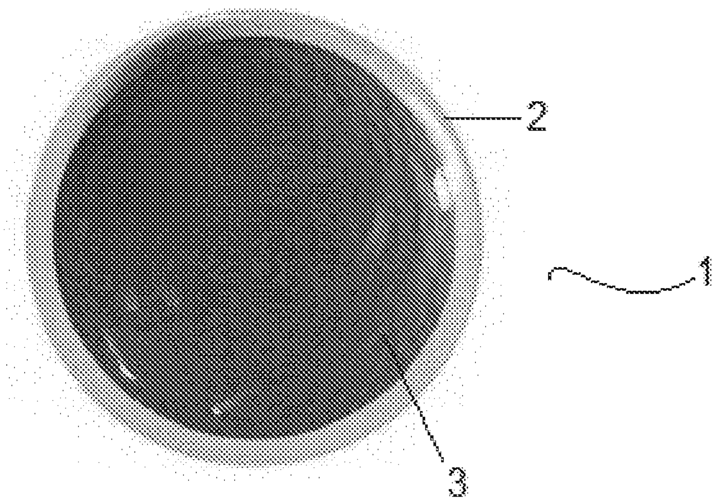
2
1
3

BREAKABLE GALENIC CAPSULE

RELATED APPLICATIONS

This application is a National Phase of PCT Patent Application No. PCT/ES2021/070112 having International filing date of Feb. 17, 2021, which claims the benefit of priority of Spain Patent Application No. P202030143 filed on Feb. 19, 2020. The contents of the above applications are all incorporated by reference as if fully set forth herein in their entirety.

FIELD AND BACKGROUND OF THE INVENTION

The present invention falls within the general field of cosmetics, and in particular, it relates to a breakable capsule (1) with a membrane (2) and core (3) suitable for releasing an active ingredient comprised in the membrane (2) both for cosmetic use and for pharmaceutical use and to the preparation process thereof.

Capsules formed by a membrane (2) and a core (3) are well known to society. Depending on the size and content thereof, they are known to serve many different purposes.

In the field of cosmetics, the use of different types of capsules containing products for application to the skin has become widespread. A problem detected in the commercial use of these capsules is that they have an insoluble membrane (2) which leaves an unusable and unpleasant residue on the skin.

In addition to capsules with a membrane (2) and core (3), there are other types of cosmetics in the form of solid capsules comprising gelled substances, which break apart when applied to the skin by the consumer, possibly leaving unabsorbed traces that also produce an unpleasant effect for the consumer. These hard capsules are known as microcapsules, and they tend to have stability problems that need to be addressed with the use of very carefully selected excipients and/or additives so as to ensure their stability over time as well as the limited size thereof.

Therefore, there is a need to provide capsules with a larger size between 7 and 30 mm and good chemical and mechanical stability wherein the capsule, once applied to the skin, reduces or does not generate residues and, at the same time, any residual trace produced by the membrane (2) can be absorbed or adsorbed by the skin. In addition, they have good stability against light and breakage.

SUMMARY OF THE INVENTION

The first aspect of the invention solves the technical problems described in the state of the art and provides spherical or essentially spherical capsules that have a size between 7 and 30 mm, the membrane (2) of which enables an adequate amount of active ingredient to be housed, at the same time preventing any visible residual trace from being left on the skin after use thereof.

The capsule (1) of the first aspect comprises a membrane (2) and core (3). The active ingredient could optionally also be located in the core (3), such that the capsule could comprise an active ingredient in the membrane (2) and another active ingredient in the core (3), thus being able to house two active ingredients that are incompatible or unstable in the presence of certain excipients within the same capsule.

Throughout the scope of the invention, active ingredient refers to a pharmaceutically or cosmetically acceptable active ingredient.

The capsule of the first aspect, as well as the membrane (2) and the core (3), can be adapted as a single-dose capsule. Said single-dose capsule would leave no visible residue once applied to the skin.

The capsule of the first aspect can be used by the consumer, putting it in contact with the skin and applying a certain pressure and subsequent rubbing on it. This causes the membrane (2) and inner core (3) components to mix, forming a homogeneous phase that can be adsorbed or absorbed by the skin in seconds, without leaving any visible traces. The capsules of the first aspect have good flexibility such that they enable the content thereof to be released in a controlled manner, without having to exert excessive force, as well as good mechanical and chemical stability over time. The capsules of the first aspect are stable up to at least 30 months under storage conditions at room temperature, between 15-25 °C.

Additionally, the capsule (1) has good stability for a period of up to 30 months under storage conditions at room temperature between 15-25 °C.

In a preferred embodiment of the first aspect of the invention, a breakable capsule (1) is referred to, characterised in that:

- the diameter of the capsule is at least 7 mm; preferably, the diameter of the capsule is between 7 and 30 mm;
- the flexibility of the capsule is up to 20% the diameter of the capsule; preferably it is up to 60%;
- the burst strength of the capsule is between 12 and 40 $gf/cm^2$, preferably the burst strength is between 20 and 30 $gf/cm^2$, more preferably it would be at least 25 $gf/cm^2$;

said capsule comprises a core (3) and an outer membrane (2) that surrounds the inner core (3), the outer membrane (2) being characterised in that:

- the membrane (2) comprises:
  - at least 20% water by weight to the total weight of the membrane (2); preferably the water content by weight in the membrane (2) is between 40% and 99.5% to the total weight of the membrane (2), more preferably between 60% and 99.5%;
  - at least 0.2% of a gelling agent and at least 0.1% of a cosmetically acceptable excipient, both measured with respect to the total weight of the membrane (2);
  - calcium, magnesium or salts thereof;
  - optionally an active ingredient in a concentration of at least 0.01% to 10% to the total weight of the membrane (2); and
  - optionally a preservative, the concentration of which in the solution can be between 0.01 and 5% and wherein the thickness of the membrane (2) is at least 150 μm; preferably at least 300 μm.

The term "gf" refers to gram-force.

When the capsule is applied to the skin with a continuous pressure of at least 15 $gf/cm^2$ and subsequent rubbing, the outer membrane (2) and the inner core (3) blend, providing a homogeneous mixture being absorbed and/or adsorbed by the skin in a few seconds, leaving the skin soft, not sticky and without visible residues.

In a preferred embodiment, the breakable capsule (1) of the first aspect comprises a membrane (2) with a concentration by weight to the total weight of the capsule (1) of between 5-30%, more preferably between 10-25%, and a core with a concentration by weight to the total weight of the capsule (1) of between 70-95%, more preferably between 90-80%. In another preferred embodiment of the first aspect, the capsule (1) comprises a membrane (2) with a weight ratio to the weight of the core (3) in a range between 1:4 and 1:8, preferably, a range between 1:4.5 and 1:6.

In the present invention, the breakable capsule refers to a capsule that is adapted to contain a cosmetically and/or pharmaceutically acceptable active ingredient therein and for use and application thereof on the skin of a subject.

In the present invention, the term "visible" residue refers to the ability of the membrane (2) of the capsule (1) to disintegrate and be adsorbed or absorbed by the skin by between 85% and 100%, preferably 100%. Therefore, once applied to the skin, no perceptible remnants would be seen.

In the present invention, the term "flexibility" refers to the ability of the membrane (2) of the capsule (1) to return to the initial shape thereof and maintain the properties thereof intact when it is pressed or crushed by the fingers of a subject without breaking.

In the present invention, "cosmetic composition" refers to the mixture of at least one active ingredient and/or one cosmetically acceptable excipient. The term "cosmetically acceptable excipient" also includes pharmaceutically acceptable excipients.

In a preferred embodiment of the first aspect of the present invention, the calcium salt of the breakable capsule (1) is selected from the group consisting of calcium ascorbate, calcium aspartate, calcium carbonate, calcium benzoate, calcium chloride, calcium citrate, calcium gluconate, calcium glycerophosphate, calcium glycinate, calcium ketoglutarate, calcium lactate, calcium phosphate, calcium sulfate, calcium tartrate, calcium pantothenate, Akomarine® PCA Complex, calcium polyglutamate crosspolymer and a mixture thereof. In another preferred embodiment of the first aspect of the present invention, the magnesium salt of the breakable capsule (1) is selected from the group consisting of magnesium hydroxide, magnesium carbonate hydroxide, calcium magnesium silicate, dolomite, magnesium chloride, magnesium citrate, magnesium alginate, magnesium glycerophosphate, magnesium glycinate, magnesium lactate, magnesium myristate, magnesium PCA or mixtures thereof.

The calcium and/or magnesium of the first aspect can be present in the form of a salt either because it is incorporated as such or because it is generated in situ. The presence of calcium, magnesium and/or salts thereof facilitate the formation and hardening of the membrane (2) as well as the thickness of the diameter thereof. At the same time, it provides the capsule with adequate flexibility for correct application thereof to the skin. Preferably, the calcium salt is selected from the group consisting of calcium ketoglutarate, calcium lactate, calcium phosphate, calcium carbonate, calcium sulfate and calcium glycinate, calcium glycerophosphate and mixtures thereof, since they help to improve control in obtaining the required membrane thicknesses.

In a preferred embodiment of the first aspect of the present invention, the capsule comprises a calcium and/or magnesium salt, wherein the calcium and/or magnesium is in a concentration of at least 0.01% to 3% to the total weight of the membrane (2). Preferably, the calcium is in a concentration of at least 0.02% to 1% to the total weight of the membrane (2).

In a preferred embodiment of the first aspect of the present invention, the gelling agent is in a range in the membrane between 0.2% and 5% to the total weight of the membrane (2). In a particular embodiment, the gelling agent can also be in the core. Preferably, the gelling agent of the invention has been selected from sodium alginate, alginine, carrageenan, gellan gums, acacia gum, guar gums, *Ceratonia siliqua* gum, cellulose gum, cellulose and derivatives, *Lessonia nigrescens* powder, agar, *Chondrus crispus*, Colophonium, dextran, dextrin, gelatin, Ghatti gum, *Himanthalia elongata* powder, maltodextrins, mannitol, mel powder, sclerotium gum, hydrolysed *Caesalpinia spinosa* gum, Xanthan gum, Pullulan, polyvinylpyrrolidone (PVP), trehalose and in general monosaccharides, disaccharides and polysaccharides, carbomer and acrylates, pectins, gelatins, *Astragalus gummifer* gum, Cassia gum, rice, tapioca, wheat, corn starches, resin, Sterculian Urens gum, silicas, Kelco-Care diutan gum, dihydroxy xanthan gum, biosaccharide gum, *Boswellia serrata* gum, *Ulva lactuca* powder and mixtures thereof. Preferably, the gelling agent of the membrane (2) is selected from the group consisting of alginine, sodium alginate, carrageenan, xanthan gum, maltodextrin and gellan gum.

In another particular embodiment of the first aspect, the active ingredient is in the membrane (2) in a concentration of 0.01% to 10% to the total weight of the membrane (2);

In another preferred embodiment of the first aspect, the core (3) comprises water and a cosmetic composition that can comprise active ingredients and/or excipients. Preferably, the concentration of active ingredients if present is in a range between 0.01% and 100% to the total weight of the core (3), preferably between 1% and 98%.

In another particular embodiment of the first aspect, the active ingredient is in the core (3) and in the membrane (2). In this way, the breakable capsule of the first aspect can comprise and release incompatible active ingredients or excipients.

In another particular embodiment of the first aspect, the active ingredient can be a cosmetic active ingredient and/or a pharmaceutical active ingredient. In a preferred embodiment, the active ingredient is selected from the group consisting of hyaluronic acid and salts thereof; vitamins, minerals, collagen, retinol, mucopolysaccharides; *Aloe vera, Aloe Barbadensis* leaf juice powder, aloe plant juices; aqueous plant extracts such as *Morinda citrifolia* leaves; oily plant extracts such as rosemary, calendula, arnica, chamomile, carrot, saturated or unsaturated fatty acids; oils, amino acids, peptides and proteins and a mixture thereof.

In a particular embodiment of the first aspect of the present invention, the type of cosmetic or pharmaceutical formulation contained in the core (3) is selected from the group consisting of powders, aqueous and oily gels, creams, ointments, serums, oils, aqueous and oily emulsions, aqueous, hydroalcoholic and oily solutions.

In the present invention, the term "excipient" refers to carriers and additives. The term "carriers" refers to specific components necessary for the formation of the cosmetic or pharmaceutical composition, both of the membrane (2) and of the core (3). The term "carrier" refers to substances that prevent a cosmetic from deteriorating or improve the appearance thereof, helping to achieve a stable, attractive product. Preferably, the additives of the present invention are selected from the list consisting of plasticisers, thickeners, emollients, foaming agents, dyes, pigments, perfumes, pH controllers, preservatives, antioxidants, moisturisers, mattifying agents, natural and synthetic sunscreens.

In a more preferred embodiment, the excipient is a cosmetically and/or pharmaceutically acceptable carrier and/or an additive. In another preferred embodiment, the cosmetically acceptable excipient is in a range between 0.2% and 10% to the total weight of the membrane.

In the context of the present invention, the cosmetically and/or pharmaceutically acceptable excipient can be a cosmetically and/or pharmaceutically acceptable carrier suitable for dissolving or mixing active ingredients, such as forming saline, aqueous, alcoholic and oily solutions; oily external phase, aqueous external phase and silicone external phase emulsions; aqueous and oily gels; and powders. Preferably, the cosmetically and/or pharmaceutically acceptable carrier is selected from the group consisting of water, thickeners, waxes, surfactants, co-emulsifiers, silicones, organic oils, mineral oils, absorbents, organic powders, inorganic powders, stabilisers, exfoliating particles, liposomes, acids and alkalis, buffers and salts, sequestrants.

In another particular embodiment of the first aspect of the present invention, the excipient is at least one plasticiser that is selected from the group consisting of propanediol, glycerol, propylene glycol of a molecular weight (Mn) between 400 and 2000, polyethylene glycol of a molecular weight (Mn) between 400 and 4000, pentylene glycol, triacetin.

In another particular embodiment of the first aspect of the present invention, the core (3) of the breakable capsule (1) comprises a cosmetic composition comprising cosmetically acceptable oils selected from a group consisting of *Prunus amygdalus dulcis, Argania spinosa, Simmondsia chinensis* seed oil, *Camellia oleifera* seed oil, *Citrus nobilis* peel oil, aloe oil or mixtures thereof, and the membrane (2) comprises excipients that are selected from the group consisting of preservatives, plasticisers, thickeners, silicones, stabilisers, antioxidants, moisturisers and surfactants, wherein the concentration of the cosmetic composition in the core can be in a range from 5-100%. Even more preferably, the excipient is at least one plasticiser that is selected from the group consisting of propanediol, glycerol, propylene glycol of a molecular weight (Mn) between 400 and 2000, polyethylene glycol of a molecular weight (Mn) between 400 and 4000, pentylene glycol, triacetin. Preferably, this particular embodiment is prepared by the process of the third aspect of the invention.

In a particular embodiment of the first aspect of the present invention, the raw materials used to prepare the membrane (2) can be all natural, without incorporating any synthetic component.

In another particular embodiment of the first aspect of the present invention, the excipient is at least one preservative that is selected from the group consisting of benzyl alcohol, dehydroacetic acid, tocopherol, glycols, pentylene glycol, hexylene glycol, benzoate and phosphate salts, ethylhexylglycerin, phenoxyethanol, etc.

In a particular embodiment of the first aspect, the breakable capsule further comprises in the outer membrane (2) and/or in the inner core (3):

at least one dye; and/or
at least one aromatic agent; and/or
at least one fragrance;
and optionally, at least one flavouring.

The process of the second aspect is known as reverse spherification.

The second aspect of the invention relates to a method for obtaining the breakable capsule (1) of the first aspect, said process comprises at least the following steps:

a) Providing a mixture comprising at least one gelling agent, one excipient and cosmetically acceptable water;
b) Providing a second mixture comprising an aqueous phase, preferably water and at least one calcium/magnesium salt, optionally an oil and an emulsifier;
c) Adding the mixture obtained in step b) to the mixture obtained in step a) in such a way that when adding the mixture of step b) to step a), the mixture of step b) precipitates on the mixture of step a) forming a solid or semi-solid sphere;
d) Adding the sphere obtained in step c) to a bath comprising at least water and/or oil.

In the present invention, the term "cosmetically acceptable water" also includes pharmaceutically acceptable water and refers to distilled, demineralised or purified water. The purified water has been previously filtered, decalcified and sterilised.

The process of the third aspect is known as spherification by encapsulation.

The third aspect of the invention relates to an alternative method to that of the second aspect, for obtaining the breakable capsule (1) of the first aspect, said process comprises at least the following steps:

a) Providing a mixture comprising at least one gelling agent, one excipient and cosmetically acceptable water;
b) Providing a second mixture comprising at least one pharmaceutically and/or cosmetically acceptable excipient and/or active ingredient, preferably the active ingredient is an essential oil or a fatty acid;
c) Simultaneously mixing the mixture of step a) and b) by using a double-walled concentric injector to provide a spherical cosmetic composition comprising the components of steps a) and b).
d) Adding the spherical cosmetic composition obtained in step c) to a solution comprising a calcium or magnesium salt until a solid sphere is formed.
e) Adding the solid sphere obtained in step d) to a bath comprising water and/or oil to obtain the spherical breakable capsule.

In a preferred embodiment of the third aspect of the invention, the method for preparing a breakable capsule (1) of the first aspect comprises the use of a double-walled concentric injector comprising dosing hoppers in order to dose the addition of the mixtures obtained in step a) and b) in step c).

In a preferred embodiment of the second and third aspects of the invention, the calcium salt is selected from the group consisting of calcium ascorbate, calcium aspartate, calcium carbonate, calcium benzoate, calcium chloride, calcium citrate, calcium gluconate, calcium glycolate, calcium ketogluconate, calcium lactate, calcium pantothenate, calcium PCA, calcium phosphate, calcium polyglutamate crosspolymer, calcium sulfate, calcium tartrate, calcium glycerophosphate, and a mixture thereof. Preferably, the calcium salt is selected from the group consisting of calcium ketoglutarate, calcium lactate, calcium phosphate, calcium carbonate, calcium sulfate, calcium glycinate, calcium glycerophosphate and mixtures thereof.

In a preferred embodiment of the third aspect of the invention, the calcium and/or magnesium salt is added in an aqueous solution wherein the concentration of the sum of both the calcium and magnesium salt in the solution is between 0.01% and 5% by weight.

BRIEF DESCRIPTION OF THE SEVERAL VIEWS OF THE DRAWINGS

FIG. 1 shows the structure of the capsule (1) of the present invention, in which the membrane (2) and the inner core (3) can be seen.

DESCRIPTION OF SPECIFIC EMBODIMENTS OF THE INVENTION

Examples

Example 1: Composition and Method for Preparing the Breakable Capsule (1) of the First Aspect by Means of the Method of the Second Aspect The components of the membrane (2) of the capsule 1 are shown in Table 1. The inner core (3) was made up of a cosmetic base that corresponded to the composition described in Table 2.

TABLE M1

Table M1: components of the membrane (2) of the capsule 1

| Functionality | Excipients/ Active ingredients | Weight % | Weight g |
|---|---|---|---|
| Solvent | Demineralised water | 97.654 | 483.27 |
| Gelling agent | Sodium alginate | 0.508 | 2.500 |
| Gelling agent | Carrageenan | 0.203 | 1.000 |
| Active ingredient | Sodium hyaluronate | 0.010 | 0.050 |
| Plasticiser | Propanediol | 0.346 | 1.700 |
| Calcium salt | Calcium lactate | 0.1 | 0.5 |
| Calcium salt | Calcium glycerophosphate | 0.01 | 0.05 |
| Preservative | Benzyl alcohol Dehydroacetic acid | 1.169 | 5.750 |

TABLE N1

Table N1: components of the core (3).

| Functionality | Excipients/ Active ingredients | Weight % | Weight g |
|---|---|---|---|
| Solvent | Demineralised water | 97.25 | 466.00 |
| Gelling agent | Xanthan Gum | 0.63 | 3.00 |
| Calcium salt | Calcium lactate | 0.4 | 2 |
| Calcium salt | Calcium glycerophosphate | 0.04 | 0.2 |
| Plasticiser | Propanediol (propylene glycol) | 0.21 | 1.00 |
| Active ingredient | Sodium hyaluronate | 0.01 | 0.05 |
| Active ingredient | *Aloe Barbadensis* leaf juice powder | 0.01 | 0.05 |
| Various dyes | White, green, purple | 0.26 | 1.24 |
| Preservative | Benzyl alcohol Dehydroacetic acid | 1.20 | 5.75 |

The Method for Preparing the Capsule (1) According to the Second Aspect

The components of Table 1a were mixed at a temperature between 30° and 40° until forming a mixture referred to as mixture A.

TABLE 1a

Table 1a: Components of mixture A of step a)

| Functionality | Excipients/ Active ingredients | Weight % | Weight g |
|---|---|---|---|
| Solvent | Demineralised water | 98.283 | 483.55 |
| Gelling agent | Sodium alginate | 0.508 | 2.500 |
| Gelling agent | Carrageenan | 0.203 | 1.000 |
| Active ingredient | Sodium hyaluronate | 0.010 | 0.050 |
| Plasticiser | Propanediol | 0.346 | 1.700 |
| Preservative Geogard ® 221 | Benzyl alcohol Dehydroacetic acid | 1.169 | 5.750 |

TABLE 1b

Table 1b: Components of mixture B of step b)

| Functionality | Excipients/ Active ingredients | Weight % | Weight g |
|---|---|---|---|
| Solvent | Demineralised water | 97.12 | 466.00 |
| Gelling agent | Xanthan Gum | 0.63 | 3.00 |
| Calcium salt | Calcium lactate | 0.52 | 2.50 |
| Calcium salt | Calcium glycerophosphate | 0.05 | 0.25 |
| Plasticiser | Propanediol | 0.21 | 1.00 |
| Active ingredient | Sodium hyaluronate | 0.01 | 0.05 |
| Active ingredient | *Aloe Barbadensis* leaf juice powder | 0.01 | 0.05 |
| Various dyes | White, green, purple | 0.26 | 1.24 |
| Preservative Geogard ® 221 | Benzyl alcohol Dehydroacetic acid | 1.20 | 5.75 |

Mixture B is prepared according to Table 1 b and is also referred to as serum. Once mixture B was prepared and at a temperature between 20°-25 °C, said mixture was added dropwise to the mixture A.

The mixture obtained in the previous step is left to rest for 15 to 45 seconds until a capsule is formed. After this time, the capsule (1) was removed and added to a container with distilled water at a temperature of 20-25°, wherein it was left to act for 1-10 minutes in order for the reaction to stop and any unwanted components to be eliminated from the capsule (1). Once the capsule is obtained, it is stored in a container containing a suitable medium and the process is repeated until the desired number of capsules is achieved. Once the process was finished, the container was stored in a dark, refrigerated place, such as a refrigerator.

It was confirmed that the capsules of Example 1 are stable at a temperature of 40 °C for at least 3 months.

The capsules of Example 1 had the following characteristics:

Burst strength: 25 gf/cm$^2$.

Capsule diameter: 10 mm

Flexibility: the diameter of the capsule can expand up to 0.42 cm (limit up to breakage of the membrane (2)), therefore, up to more than 400% of its diameter Total weight: 0.47 g Weight of the core (3): 0.37 g (79%)

Weight of the membrane (2): 0.10 g (21%)

Thickness of the membrane (2): 550 microns

Internal volume: 0.52 ml (including membrane (2))/0.38 ml (without membrane (2))

Example 2: Capsule 2 and Method for Preparing the Capsule (1)2 by Means of the Process of the Second Aspect of the Invention The components of the membrane (2) of the capsule (1)2 are shown in Table M2.

The inner core (3) was made up of the components and quantities of Table N1.

TABLE M2

Table M2: components of the membrane (2) of the capsule (1)2

| Functionality | Excipients/ Active ingredients | Actual weight % | Actual weight g |
|---|---|---|---|
| Solvent | Demineralised water | 96.3 | 473.8 |
| Gelling agent | Sodium alginate | 0.62 | 3.00 |
| Calcium salt | Calcium lactate | 0.41 | 2 |
| Calcium salt | Calcium glycerophosphate | 0.04 | 0.2 |
| Gelling agent | Maltodextrin | 1.22 | 6.00 |
| Active ingredient | Sodium hyaluronate | 0.01 | 0.05 |
| Flexibility | Propanediol | 0.26 | 1.25 |
| Preservative | Benzyl alcohol | 1.18 | 5.75 |
| Geogard ® 221 | Dehydroacetic acid | | |

TABLE N1

Table N1: components of the core (3) of capsule (1)2.

| Functionality | Excipients/ Active ingredients | Weight % | Weight g |
|---|---|---|---|
| Solvent | Demineralised water | 97.25 | 466.00 |
| Gelling agent | Xanthan Gum | 0.63 | 3.00 |
| Calcium salt | Calcium lactate | 0.4 | 2 |
| Calcium salt | Calcium glycerophosphate | 0.04 | 0.2 |
| Plasticiser | Propanediol | 0.21 | 1.00 |
| Active ingredient | Sodium hyaluronate | 0.01 | 0.05 |
| Active ingredient | *Aloe Barbadensis* leaf juice powder | 0.01 | 0.05 |
| Various dyes | White, green, purple | 0.26 | 1.24 |
| Preservative | Benzyl alcohol | 1.20 | 5.75 |
| Geogard ® 221 | Dehydroacetic acid | | |

To prepare the capsule 1(2), the same method of preparation as in Example 1 was followed. To do so, the components of mixture A were used, as described in Table 2a.

TABLE 2a

Table 2a: Components of mixture A of step a)

| Functionality | Excipients/ Active ingredients | Actual weight % | Actual weight g |
|---|---|---|---|
| Solvent | Demineralised water | 96.7 | 476 |
| Gelling agent | Sodium alginate | 0.62 | 3.00 |
| Gelling agent | Maltodextrin | 1.22 | 6.00 |
| Active ingredient | Sodium hyaluronate | 0.01 | 0.05 |
| Flexibility | Propanediol | 0.26 | 1.25 |
| Preservative | Benzyl alcohol | 1.18 | 5.75 |
| Geogard ® 221 | Dehydroacetic acid | | |

Components of mixture B that are used are the same as those described in Table 1b (Example 1)

The capsules (1)2 had the following characteristics:

Burst strength: 35 gf/cm$^2$.

Diameter: 10 mm

Flexibility: the diameter of the capsule (1) can expand up to 0.48 cm (limit up to breakage of the membrane (2)). Therefore, up to 480% of its diameter Total weight: 0.49 g Weight of the core (3): 0.37 g (77%)

Weight of the membrane (2): 0.12 g (23%)

Thickness of the membrane (2): 600 microns

Internal volume: 0.52 ml (including membrane (2))/0.37 ml (without membrane (2))

Example 3: Method for Preparing the Capsule (1)3 by Means of the Technique of the Method of the Third Aspect of the Invention This process required the use of a double-walled concentric injector with the corresponding hoppers thereof to correctly dose the drip.

1—Membrane (2)

The components of the membrane (2) of the capsule 3 are shown in Table M3.

TABLE M3

Table M3: components of the membrane (2) of the capsule (1)3.

| Functionality | Excipients/ Active ingredients | Weight % | Weight g |
|---|---|---|---|
| Solvent | Demineralised water | 97.75 | 481.00 |
| Gelling agent | Sodium alginate | 0.56 | 2.75 |
| Gelling agent | Gellan gum LA | 0.06 | 0.28 |
| Active ingredient | *Aloe Barbadensis* leaf juice powder | 0.01 | 0.05 |
| Plasticiser | Propanediol | 0.30 | 1.50 |
| Calcium salt | Calcium lactate | 0.182 | 0.9 |
| Calcium salt | Calcium glycerophosphate | 0.02 | 0.1 |
| Preservative | Benzyl alcohol | 1.17 | 5.75 |
| Geogard ® 221 | Dehydroacetic acid | | |

2—Core (3)

The core of Example 3 is a complex cosmetic oil. The components of said oil are described in Table N3.

TABLE N3

Table N3: components of the core (3) N3.

| Functionality | Excipients/ Active ingredients | Weight % | Weight g |
|---|---|---|---|
| Oil | *Prunus Amygdalus Dulcis* Oil (sweet almond oil) | 83 | 415 |
| Oil | *Argania Spinosa* Oil (argan oil) | 4 | 20 |
| Oil | *Simmondsia Chinensis* seed oil (Jojoba seed oil) | 10 | 50 |
| Oil | *Camellia Oleifera* Seed Oil | 1 | 5 |
| Oil | *Citrus Nobilis* Peel (mandarin peel oil) | 1.5 | 7.5 |
| Antioxidant | *Glycine Soja* Oil, Tocopherol, Beta-sitosterol, squalene | 0.5 | 2.5 |

Process for Preparing the Capsule (1)3, According to the Third Aspect of the Invention.

The compounds forming part of the membrane (2), Table M3, with the exception of the calcium salts, were homogeneously mixed at a temperature between 30 °C and 40 °C. These compounds are listed below in Table Mixture 3a.

TABLE

| Mixture 3a<br>Table Mixture 3a: mixture of the components that are added to the mixture 3a of step a) | | |
|---|---|---|
| Functionality | Excipients/<br>Active ingredients | Weight<br>in g |
| Solvent | Demineralised water | 482.00 |
| Gelling agent | Sodium alginate | 2.75 |
| Gelling agent | Gellan Gum LA | 0.28 |
| Active ingredient | *Aloe Barbadensis* leaf juice powder | 0.05 |
| Plasticiser | Propanediol | 1.50 |
| Preservative | Benzyl alcohol<br>Dehydroacetic acid | 5.75 |

The components of the mixture 3a were mixed in a temperature range between 20°–25 °C until a homogeneous mixture was obtained. Subsequently, they were placed in the hopper of the outer chamber of a double-walled concentric injector. Then the mixture of the components of Table N3 was prepared at a temperature between 20°–25 °C until a homogeneous mixture was obtained. Once said oil was obtained, it was placed in the hopper connected to the inner chamber of the double-walled concentric injector.

The components of the tables, Mixture 3a and N3, are simultaneously added from the injector, from a determined height of between 0.1 cm and 2 cm, in the bath A. Bath A comprises an aqueous solution of a calcium salt, as described in Table 4. The components of the reagent bath (bath A) are shown in Table 4.

TABLE 4

| Table 4: components of bath A | | | |
|---|---|---|---|
| | Excipients/ | Weight | |
| Functionality | Active ingredients | % | g |
| Solvent | Demineralised water | 99.5 | 995 |
| Calcium salt | Calcium lactate,<br>Calcium glycerophosphate.<br>Ratio 10:1 | 0.5 | 5 |

The contents of the previous step were left in the bath for 10 to 20 seconds until a capsule (1) was formed. After this time, the capsule (1) was removed from bath A and added to a container with distilled water at a temperature of 20-25° (bath B), wherein it was left to act for 1-10 minutes in order for the reaction to stop and the capsule (1) to be obtained clean of other unwanted components. Once the capsule is obtained, it is stored in a container containing a suitable medium and the process is repeated until the desired number of capsules is achieved.

Once the process was finished, the appropriate controls were carried out. The capsules were then stored in a suitable container which contains a suitable stability medium, as mentioned above, under temperature and humidity conditions that keep them stable until the time of individual packaging.

The capsules 3 had the following characteristics:

Burst strength: 32 gf/cm$^2$.

Diameter: 10 mm

Flexibility: the diameter of the capsule can expand up to 6 mm (limit up to breakage of the membrane (2)). Up to 60% of its diameter.

Total weight: 0.38 g

Weight of the core (3): 0.29 g (75%)

Weight of the membrane (2): 0.10 g (25%)

Thickness of the membrane (2): 500 microns

Internal volume: 0.52 ml (including membrane (2))/0.39 ml (without membrane (2))

Example 4: Breakable Capsule (1) Composition of the First Aspect Prepared According to the Method of Preparation of the Second Aspect (Reverse Esterification)

| MEMBRANE COMPOSITION | | | |
|---|---|---|---|
| Functionality | Excipients/<br>Active ingredients | % by weight in the capsule | % by weight in the membrane |
| Solvent | Aqua | 16.437 | 97.24 |
| Gelling agent | Algin | 0.077 | 0.45 |
| Gelling agent | Maltodextrin (bio) | 0.102 | 0.60 |
| Flexibility | Propanediol | 0.051 | 0.30 |
| Calcium salt | Calcium Lactate | 0.056 | 0.33 |
| Calcium salt | Calcium Glycerophosphate | 0.037 | 0.21 |
| Active ingredient | Hyaluronic Acid | 0.002 | 0.01 |
| Preservative | Benzyl Alcohol,<br>Dehydroacetic Acid | 0.153 | 0.90 |
| Gelling agent | Xanthan Gum | 0.085 | 0.50 |
| | TOTAL | 17.000 | 100 |

| CORE COMPOSITION | | | |
|---|---|---|---|
| Functionality | Excipients/<br>Active ingredients | % by weight in the capsule | % by weight in the core |
| Active ingredient | INCI Natural Mint Hand Gel Solution* | 82.544 | 99.45 |
| Calcium salt | Calcium Lactate | 0.274 | 0.33 |
| Calcium salt | Calcium Glycerophosphate | 0.183 | 0.22 |
| | TOTAL | 83.000 | 100 |

The INCI Natural Mint Hand Gel Solution* comprises: Water, propanediol, *Aloe barbadensis* leaf juice, Leuconostoc/Radish Root Ferment Filtrate. Benzyl alcohol, C13-15 alkane, decyl glucoside, succinoglycan, Peppermint oil, citric acid, dehydroacetic acid, indigo dye leaf extract, mica, tin oxide, titanium oxide.

Capsule weight: 0.28 g. Membrane Weight 0.0477 g and Core Weight 0.233 g.

Brust strength: 25 gf/cm$^2$

The burst strength can be measured by a texture analyser.

To carry out the burst strength test, a 2 mm cylinder probe was used to determine burst strength and/or compression point of the membrane at the point of contact. The capsule is deposited perpendicular to the downward direction of the cylindrical probe which penetrates and breaks the sample at a constant speed. The texture analyser measures the force required to break the capsule.

Stability Controls of the Capsules 1, 2 and 3.

Once the capsules were prepared, the stability thereof was determined; to do so, different strength assays and aging tests were performed in the laboratory.

Stability tests at different temperatures: These tests measured the stability of the capsules of Examples 1, 2 and 3 as a cosmetic. Duration of the stability test was between 12 and 14 weeks.

Room temperature: Between +18° and +25 °C.

Aim: To evaluate the stability of the capsules at room temperature

Results at room temperature: The capsules showed no change in any of the cases

Aim: To age the product in an accelerated manner, at 40 °C in the oven, in order to ensure the stability thereof at temperature over real time. The temperature was maintained constant during the 12 or 14 weeks at 40 °C.

Results: The capsules do not undergo any type of change. Bleeding of the colours towards the external liquid also does not appear, meaning that they remain stable throughout the entire process of the study.

Aim: To test the stability of the product at low temperatures, +4 °C and +8 °C.

Results: The capsules do not undergo any type of change

Light stability tests:

Aim: Light tests are essential for all products whose final packaging is transparent or translucent. It was observed whether there were changes in the behaviour of the product in terms of the stability or physical appearance thereof against 2 types of light.

a) Natural (without direct solar radiation) and b) Artificial “fluorescent”, the type of light usually found in commercial buildings.

Results: The capsules do not undergo any type of change. The capsules behave in a stable manner against the two types of lights tested.

In conclusion, the capsules of the first aspect of the invention and those obtained from the second and third aspects were stable to breakage, texture and the application test thereof, especially after 30 weeks at room temperature between 18-25 °C, preferably 14 weeks, and/or after 12 weeks at 40 °C, preferably 8 weeks, and no type of alteration was observed Structural and Mechanical Stability TEST of the Membrane If the membrane remains stable over time and under forced temperature conditions, it must be able to disintegrate when pressure is applied with the fingers and be able to mix with the core.

The following is also analysed:

A—Dissolution and mixing time of the membrane and the core once pressure is exerted and until a homogeneous mixture is obtained in which the products form a single phase.

Method:

1.—A sample is placed in the palm of the hand.

2.—When a digital stopwatch is started, the capsule (1) is broken with the other hand and the contents rubbed until the film of the membrane disintegrates until forming a homogeneous mixture in a single phase together with the core.

3.—The digital stopwatch is observed and the time is measured. (Time A) Time A is between 5 and 25 seconds, preferably less than 15 seconds.

B—Acting time on the skin after application thereof; the action can be absorption or adsorption depending on the excipients or active ingredients of the new phase, by at least 85% and preferably 100%.

The mixture obtained at the end of part A is applied to the desired area of the skin as an ordinary cosmetic and it is necessary to wait until the skin shows the cosmetic's intended effect. Mainly, it is observed that there are no product traces on the skin and the product is not sticky.

The digital stopwatch is observed and the time is measured. (Time B). Time B is between 20 and 120 seconds, preferably between 20 and 60 seconds, more preferably between 20-40 seconds.

The sum of the times will give us the total time, which will be the sum of the dissolution and mixing time of the membrane and the core once pressure is exerted and until a homogeneous mixture is obtained in which the products form a single phase, time A, and the time in which the product is absorbed or adsorbed by the senses (vision and touch) on the skin, time B. The total time (time A+B) is between 25 and 150 seconds, preferably between 25 and 85 seconds, more preferably between 25 and 45 seconds.

The invention claimed is:

1. A breakable capsule (1) comprising:

the diameter of the capsule is between 7 mm and 30 mm;

the flexibility of the capsule is configured so that there is up to a 60% enlargement in diameter of the capsule before breakage of the membrane;

the burst strength of the capsule is from 25 to 35 gr/cm$^2$;

said capsule comprises a core (3) and an outer membrane (2) that surrounds the inner core (3), the outer membrane (2) comprising:

at least 96% and up to 99.5% water by weight to the total weight of the membrane;

at least 0.2% of a gelling agent and at least 0.1% of a cosmetically acceptable excipient, to the total weight of the membrane;

calcium, magnesium or salts thereof; and wherein the thickness of the membrane (2) is at least 150 μm.

2. The breakable capsule (1) according to claim 1, wherein the calcium salt is selected from the group consisting of calcium ascorbate, calcium aspartate, calcium carbonate, calcium benzoate, calcium chloride, calcium citrate, calcium gluconate, calcium glycerophosphate, calcium ketoglutarate, calcium lactate, calcium phosphate, calcium sulfate, calcium glycinate, calcium tartrate, calcium pantothenate, calcium polyglutamate crosspolymer, calcium glycerophosphate, and a mixture thereof, and/or the magnesium salt are selected from the group consisting of magnesium hydroxide, magnesium carbonate hydroxide, magnesium calcium silicate, dolomite, magnesium chloride, magnesium citrate, magnesium alginate, magnesium glycerophosphate, magnesium glycinate, magnesium lactate, magnesium myristate, magnesium PCA or mixtures thereof.

3. The breakable capsule (1) according to claim 1, wherein the amount of calcium and/or magnesium is in a concentration of at least 0.01% to 3% to the total weight of the membrane.

4. The breakable capsule (1) according to claim 1, wherein the cosmetic composition comprises an active ingredient that is a cosmetically acceptable oil, selected from a group consisting of *Prunus Amygdalus Dulcis, Argania spinosa, Simmondsia chinensis* seed oil, *Camellia oleifera* seed oil, aloe oil, *Citrus nobilis* peel oil and mixtures thereof.

5. The breakable capsule (1) according to claim 1, wherein the percentage by weight of the membrane (2) to the weight of the capsule (1) is between 5-30% and/or the percentage by weight of the core (3) to the weight of the capsule (1) is in a range between 70-95%.

6. The breakable capsule (1) according to claim 1, wherein the active ingredient is in the core (3), or wherein the active ingredient is in the core (3) and in the membrane (1).

7. The breakable capsule (1) according to claim 1, wherein the gelling agent of the membrane (2) is selected from the group consisting of sodium alginate, carrageenan, gellan gum, acacia gum, guar gum, *Ceratonia siliqua* gum, sclerotium gum, hydrolysed *Caesalpinia spinosa* gum, xanthan gum, cellulose gum, cellulose and cellulose derivatives, *Lessonia nigrescen* powder, Agar, *Chondrus crispus*, diutan gum, dihydroxy xanthan gum, biosaccharide gum, *Boswellia serrata* gum Colophonium, dextran, dextrin, gelatin, Ghatti gum, *Himanthalia elongata* powder, maltodextrins, mannitol, mel powder, xanthan gum, Pullulan, trehalose, monosaccharides, disaccharides, polysaccharides, polyvinylpyrrolidone, carbomer; acrylates, pectins, gelatins, *Astragalus* gum, Cassia gum; rice, tapioca, wheat and corn starch, Rosin, Sterculian Urens gum, silica, *Ulva lactuca* powder and mixtures thereof.

8. The breakable capsule (1) according to claim 1, wherein the active ingredient is selected from the group consisting of hyaluronic acid and salts thereof; mucopolysaccharides; *Aloe vera, Aloe Barbadensis* leaf powder or juice and aloe plant juices; aqueous plant extracts, oily plant extracts; amino acids, peptides and proteins; vitamins, minerals and a mixture thereof.

9. The breakable capsule (1) according to claim 1, wherein the core or the cosmetically acceptable excipient is a cosmetically acceptable carrier suitable for forming at least one of saline, aqueous, alcoholic and oily solutions; oily external phase, aqueous external phase and silicone external phase emulsions; aqueous and oily gels; and powders.

10. The breakable capsule (1) according to claim 1, wherein the excipient is at least one plasticiser that is selected from the group consisting of propanediol, glycerol, propylene glycol of a molecular weight (Mn) between 400 and 2000, polyethylene glycol of a molecular weight (Mn) between 400 and 4000, pentylene glycol and triacetin.

11. The breakable capsule (1) according to claim 1, wherein the excipient is at least one preservative that is selected from the group consisting of benzyl alcohol, dehydroacetic acid, glycerin soja oil, tocopherol, glycols, benzoate and phosphate salts, ethylhexylglycerin, and phenoxyethanol.

12. The breakable capsule (1) according to claim 1, wherein the outer membrane (2) and/or the inner core (3) comprise: at least one dye; and/or at least one aromatic agent.

13. The breakable capsule (1) according to claim 1, wherein the membrane (2) disintegrates by rubbing on the skin while the components thereof are absorbed or adsorbed by the skin by at least 85%, both processes occurring in a total time between 25 and 150 seconds.

14. The breakable capsule (1) according to claim 1, which is stable for at least 30 weeks at room temperature between 15-25 °C, or which is stable for at least 12 weeks at a temperature of 40 °C.

15. The breakable capsule (1) according to claim 1, wherein the burst strength of the capsule is 32 $gr/cm^2$, the diameter of the capsule is 10 mm, and the thickness of the membrane (2) is 500 microns.

16. A breakable capsule (1) comprising:

the diameter of the capsule is between 7 mm and 30 mm;

the flexibility of the capsule is configured so that there is up to a 60% enlargement in diameter of the capsule before breakage of the membrane;

the burst strength of the capsule is between 12 and 40 $gf/cm^2$;

said capsule comprises a core (3) and an outer membrane (2) that surrounds the inner core (3), the outer membrane (2) comprising:

between 60% and 99.5% water by weight to the total weight of the membrane;

at least 0.2% of a gelling agent and at least 0.1% of a cosmetically acceptable excipient, to the total weight of the membrane;

calcium, magnesium or salts thereof; and wherein the thickness of the membrane (2) is at least 150 μm.

* * * * *